(12) United States Patent
Hayashi

(10) Patent No.: US 7,732,605 B2
(45) Date of Patent: Jun. 8, 2010

(54) SYNTHESIS OF DIKETOPIPERAZINES

(75) Inventor: Yoshio Hayashi, Shiga (JP)

(73) Assignee: Nereus Pharmaceuticals, Inc., San Diego, CA (US)

( * ) Notice: Subject to any disclaimer, the term of this patent is extended or adjusted under 35 U.S.C. 154(b) by 1043 days.

(21) Appl. No.: 11/390,326

(22) Filed: Mar. 27, 2006

(65) Prior Publication Data

US 2006/0235226 A1  Oct. 19, 2006

Related U.S. Application Data

(60) Provisional application No. 60/666,336, filed on Mar. 29, 2005, provisional application No. 60/730,759, filed on Oct. 27, 2005.

(51) Int. Cl.
*C07D 241/04* (2006.01)
*C07D 413/00* (2006.01)
*C07D 417/00* (2006.01)
*C07D 403/00* (2006.01)

(52) U.S. Cl. .................. 544/369; 544/370; 544/385

(58) Field of Classification Search ............... 544/369, 544/370, 385
See application file for complete search history.

(56) References Cited

U.S. PATENT DOCUMENTS

| 5,891,877 | A  | 4/1999  | Brocchini et al. |
| 6,358,957 | B1 | 3/2002  | Fukumoto et al. |
| 6,972,289 | B1 | 12/2005 | Kanzaki et al. |
| 2004/0102454 | A1 | 5/2004 | Hayashi et al. |
| 2006/0167010 | A1 | 7/2006 | Hayashi et al. |
| 2006/0217553 | A1 | 9/2006 | Hayashi et al. |

FOREIGN PATENT DOCUMENTS

| EP | 0 655 060 B1 | 1/1998 |
| WO | WO 99/38844 | 8/1999 |
| WO | WO 2004/054498 A2 | 7/2004 |

OTHER PUBLICATIONS

Siwicka, et al., Diastereodivergent Synthesis of 2,5-diketopiperazine Derivatives of B-carboline and Isoquinoline from L-amino Acids, Tetrahedron: Asymmetry 16, 975-993 (2005).*
Akerlund et al., "Diketopiperazine-Based Polymers from Common Amino Acids," Journal of Applied Polymer Science (2000), 78 (12), 2213-2218.
Goldfarb et al., "Synthesis of β-2-thienylalanine" Izvestiya Akademii Nauk SSSR, Seriya Khimicheskaya, pp. 98-100 (1958), as abstracted by CAPLUS.
Hayashi, et al., "Total Synthesis of Anti-microtubule Diketopiperazine Derivatives: Phenylahistin and Aurantiamine," *J. Org. Chem.* 2000, 65: 8402-8405.
Kanoh et al., "Synthesis and Biological Activities of Phenylahistin Derivatives," Bioorganic & Medicinal Chemistry, 7: 1451-1457 (1999).
Kopple et al., "A Convenient Synthesis of 2,5-Piperazinediones 1a," *The Journal of Organic Chemistry*, 33: 862-864 (1967).
Niemann et al., "The Synthesis of the Three Isomeric dl-β-Pyridylalanines" Journal of the American Chemical Society, vol. 64(7), pp. 1678-1682 (1942).
Nitecki et al., "A Simple Route to Sterically Pure Diketopiperazines1," *The Journal of Organic Chemistry*, 33: 864-866 (1968).
Saito et al., Synthesis of novel octahydro-1, 5-imino-3-benzazocin-4, 7, 10-trione derivatives having a methyl group at the C-2 position as ABC ring models of saframycins. *Chemical & Pharmaceutical Bulletin* (1997), 45(7), 1120-1129.
Siwicka, et al., "Diastereodivergent synthesis of 2,5-diketopiperazine derivatives of β-carboline and isoquinoline from L-amino acids," Tetrahedron: *Asymmetry* 16 (2005) 975-993.
Zawadzka, et al., "Diastereoselective Synthesis of 1-Benzyltetrahydroisoquinoline Derivatives from Amino Acids by 1,4 Chirality Transfer," *Eur. J. Org. Chem.* 2003, 2443-2453.
International Search Report for International Appln. No. PCT/US2006/011206, mailed Dec. 6, 2006.

* cited by examiner

*Primary Examiner*—James O Wilson
*Assistant Examiner*—Erich A Leeser
(74) *Attorney, Agent, or Firm*—Knobbe Martens Olson & Bear LLP

(57) ABSTRACT

Disclosed herein are methods for synthesizing diketopiperazines with enantiomeric excess by inducing cyclization of an α-keto acid with an acid catalyst.

8 Claims, No Drawings

SYNTHESIS OF DIKETOPIPERAZINES

RELATED APPLICATIONS

This application claims the benefit of U.S. Provisional Application No. 60/666,336, filed on Mar. 29, 2005 and U.S. Provisional Application No. 60/730,759, filed on Oct. 27, 2005, both of which are incorporated herein by reference in their entirety.

BACKGROUND OF THE INVENTION

1. Field of the Invention

The present invention relates to the fields of chemistry and medicine. More particularly, the present invention relates to the synthesis of diketopiperazines and related compounds.

2. Description of the Related Art

It has been reported that tryprostatins A and B (which are diketopiperazines consisting of proline and isoprenylated tryptophan residues), and five other structurally-related diketopiperazines, inhibited cell cycle progression in the M phase, see Cui, C. et al., 1996 *J Antibiotics* 49:527-33; Cui, C. et al. 1996 *J Antibiotics* 49:534-40, and that these compounds also affect the microtubule assembly, see Usui, T. et al. 1998 *Biochem J* 333:543-48; Kondon, M. et al. 1998 *J Antibiotics* 51:801-04. It is known that when an abnormality arises in the control mechanism of the cell cycle, cancer or an immune disorder may occur. Accordingly, substances that regulate the cell cycle may be effective antitumor agents and immune suppressors. Thus, new methods for producing eukaryotic cell cycle inhibitors are needed as antitumor and immune-enhancing compounds, and should be useful in the treatment of human cancer as chemotherapeutic, anti-tumor agents. See, e.g., Roberge, M. et al., Cancer Res. (1994), 54, 6115-21.

Diketopiperazine-type metabolites have been isolated from various fungi as mycotoxins, see Horak R. M. et al., 1981 *JCS Chem Comm* 1265-67; Ali M. et al., 1898 Toxicology Letters 48:235-41, or as secondary metabolites, see Smedsgaard J. et al., 1996 *J Microbiol Meth* 25:5-17. The chemical synthesis of one type of diketopiperazine-type metabolite, phenylahistin, has been described by Hayashi et al. in *J. Org. Chem.* (2000) 65, page 8402.

Monodehydro-diketopiperazines have also been isolated from various organisms (e.g., from *Penicillium piscarium*, Kozlovsky et al., *Product Lett.* (2000) 14, 333; from *Anthosigmella aff. Raromicrosclera*, Tsukamoto et al. *Tetrahedron* (1995) 51, 6687; from *Streptomycesnoursei*, Shin et al. *Heterocycles* (1980) 14, 1767; Viridamine from *Penicillium viridicatum*, Holzafpel et al. *South Afr. J. Chem.* (1977) 30, 197; (−)-Phenylahistin from *Aspergillus ustus*, Kanoh et al. *Bioorg Med. Chem.* (1999) 7, 1451; and Aurantiamine from *Penicillium aurantiogriseum*, Larsen et al. *Phytochemistry* (1992) 31, 1613).

With the incidences of cancer on the rise, there exists a particular need for chemically producing a class of substantially purified diketopiperazine-type metabolite-derivatives having animal cell-specific proliferation-inhibiting activity and high antitumor activity and selectivity. There is therefore a particular need for an efficient method of synthetically producing substantially purified diketopiperazine-type metabolite-derivatives.

Prior syntheses of monodehydro-2,5-diketopiperazines have been problematic due to racemization at the side chain site opposite the dehydro side chain site. Thus, there is a need for synthetic methods for producing stereochemically pure diketopiperazines.

SUMMARY OF THE INVENTION

A method is disclosed for preparing a compound of formula I:

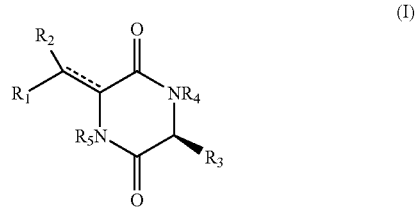

including reacting an acid catalyst with a compound of formula II in such a manner so as to produce the compound of formula I with an enantiomeric excess greater than about 50%:

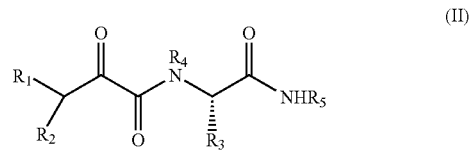

wherein:

$R_1$, $R_2$, and $R_3$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, alkoxy, acyl, arylalkyl, heteroarylalkyl, alkyloxycarbonyloxy, ester, arylalkoxy, alkoxy, or alkylthio; mono-substituted, poly-substituted or unsubstituted variants of the following residues: acyloxy, aryloxycarbonyloxy, cycloalkyl, cycloalkenyl, cycloalkoxy, aryl, heteroaryl, heterocycloalkyl, carbonyl, carbonylacyl, amino, aminocarbonyl, amide, aminocarbonyloxy, nitro, azido, phenyl, hydroxyl, arylthio, oxysulfonyl, carboxy, and cyano;

$R_4$ and $R_5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, aryl-$C_{1-6}$-alkyl, or $C_{2-6}$ hydroxyalkyl; mono-substituted, poly-substituted or unsubstituted variants of the following residues: $C_{3-8}$ cycloalkyl, —C(O)—$C_{5-6}$ aryl substituted with $C_{1-3}$ alkyl or halo, $C_{5-6}$ aryl, $C_{5-6}$ heteroaryl, $C_{5-6}$ cycloalkyl, and $C_{5-6}$ heterocycloalkyl;

any bond represented by a dashed and solid line represents a bond selected from the group consisting of a single bond and a double bond; and any carbon-carbon double bond has a configuration selected from the group consisting of cis and trans.

In some embodiments, the acid catalyst is selected from the group consisting of acetic acid, trifluoroacetic acid, methanesulfonic acid, p-toluenesulfonic acid, and trifluoromethanesulfonic acid. In one embodiment, the enantiomeric excess is greater than about 80%. In another embodiment, the enantiomeric excess is greater than about 90%.

In some embodiments, the compound of formula I is selected from the group consisting of:

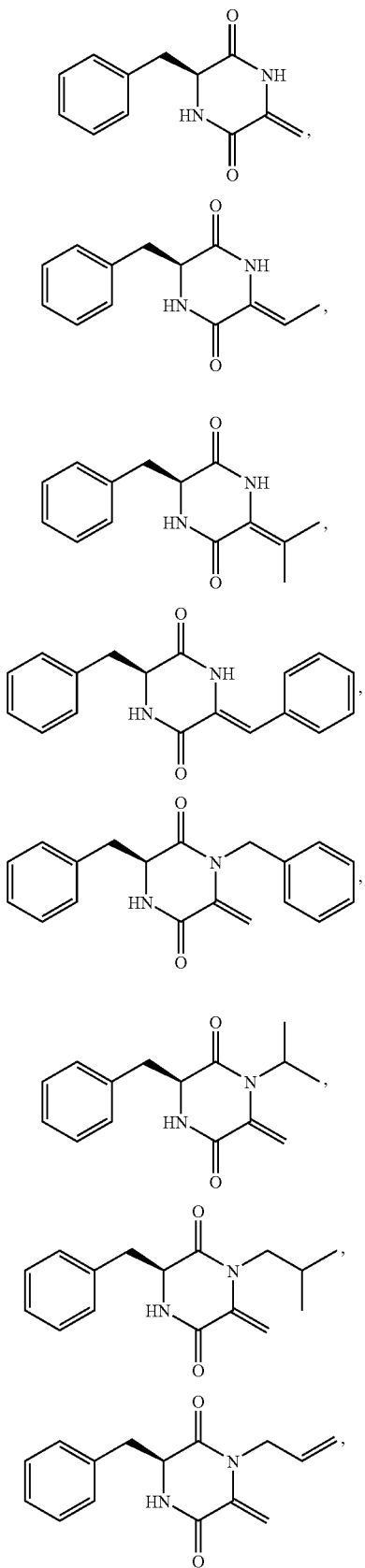
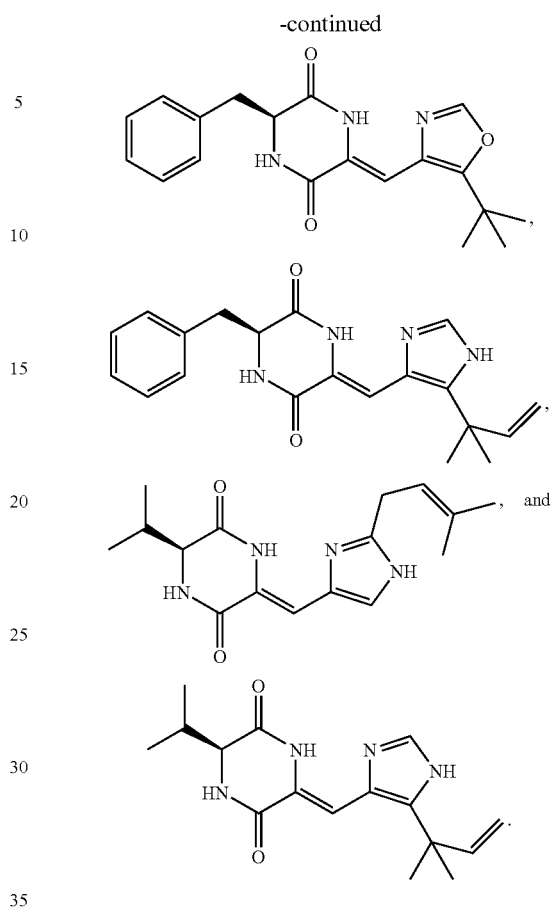
A method is disclosed for preparing a compound of formula II:
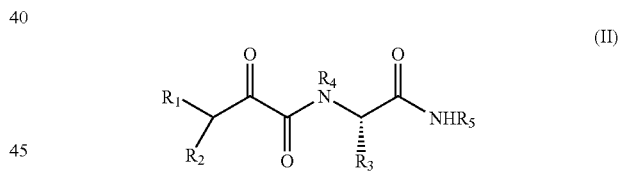
(II)
including performing the following reaction:
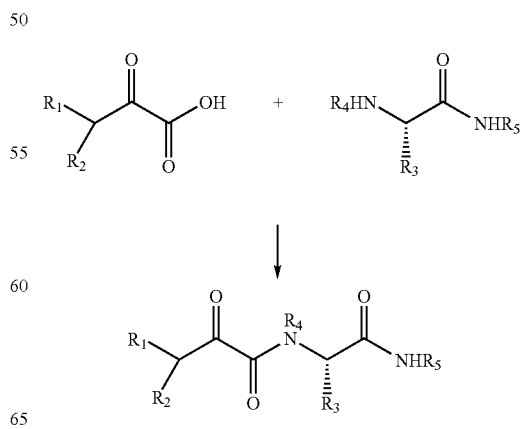

wherein:

$R_1$, $R_2$, and $R_3$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, alkoxy, acyl, arylalkyl, heteroarylalkyl, alkyloxycarbonyloxy, ester, arylalkoxy, alkoxy, or alkylthio; mono-substituted, poly-substituted or unsubstituted variants of the following residues: acyloxy, aryloxycarbonyloxy, cycloalkyl, cycloalkenyl, cycloalkoxy, aryl, heteroaryl, heterocycloalkyl, carbonyl, carbonylacyl, amino, aminocarbonyl, amide, aminocarbonyloxy, nitro, azido, phenyl, hydroxyl, arylthio, oxysulfonyl, carboxy, and cyano; and $R_4$ and $R_5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, aryl-$C_{1-6}$-alkyl, or $C_{2-6}$ hydroxyalkyl; mono-substituted, poly-substituted or unsubstituted variants of the following residues: $C_{3-8}$ cycloalkyl, —C(O)—$C_{5-6}$ aryl substituted with $C_{1-3}$ alkyl or halo, $C_{5-6}$ aryl, $C_{5-6}$ heteroaryl, $C_{5-6}$ cycloalkyl, and $C_{5-6}$ heterocycloalkyl.

In some embodiments of the compounds of formulae I and II, $R_1$, $R_2$, and $R_3$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, arylalkyl, heteroarylalkyl; and mono-substituted, poly-substituted or unsubstituted variants of the following residues: cycloalkyl, cycloalkenyl, aryl, heteroaryl, or heterocycloalkyl.

In other embodiments of the compounds of formulae I and II, $R_1$, $R_2$, and $R_3$ are separately selected from the group consisting of hydrogen; mono-substituted, poly-substituted or unsubstituted, straight or branched chain variants of the following residues: $C_1$-$C_{24}$ alkyl, arylalkyl, heteroarylalkyl; and mono-substituted, poly-substituted or unsubstituted variants of the following residues: cycloalkyl, aryl, heteroaryl, or heterocycloalkyl.

In still other embodiments of the compounds of formulae I and II, $R_1$, $R_2$, and $R_3$ are separately selected from the group consisting of hydrogen, methyl, methylene, and mono-substituted, poly-substituted or unsubstituted variants of the following residues:

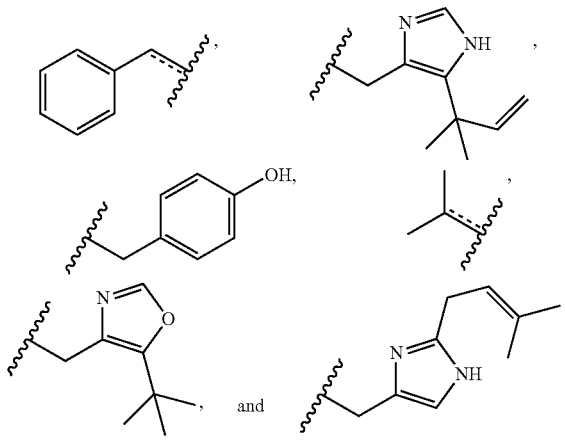

Disclosed herein are reactions and protocols of Appendices A, B, and C.

DETAILED DESCRIPTION OF THE PREFERRED EMBODIMENT

The reaction of α-ketoester with Boc-NH$_2$ in the presence of a catalytic amount of TsOH under reflux conditions forms Boc-dehydroamino acid esters. S. Gladiali, L. Pinna, *Tetrahedron: Asymmetry*, 2, 623 (1991), which is incorporated herein by reference in its entirety. It has been discovered that a similar synthetic scheme may be used in an intramolecular reaction to induce cyclization and formation of diketopiperazines with little or no racemization. Accordingly, in one embodiment, a method of synthesizing stereochemically pure diketopiperazines is provided. In one embodiment, a compound of formula I is synthesized:

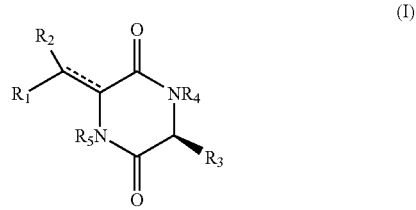

(I)

by reacting an acid catalyst with a compound of formula II in such a manner so as to produce an enantiomeric excess greater than about 50%:

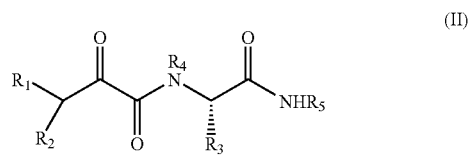

(II)

wherein $R_1$, $R_2$, and $R_3$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, alkoxy, acyl, arylalkyl, heteroarylalkyl, alkyloxycarbonyloxy, ester, arylalkoxy, alkoxy, or alkylthio; mono-substituted, poly-substituted or unsubstituted variants of the following residues: acyloxy, aryloxycarbonyloxy, cycloalkyl, cycloalkenyl, cycloalkoxy, aryl, heteroaryl, heterocycloalkyl, carbonyl, carbonylacyl, amino, aminocarbonyl, amide, aminocarbonyloxy, nitro, azido, phenyl, hydroxyl, arylthio, oxysulfonyl, carboxy, and cyano;

$R_4$ and $R_5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, aryl-$C_{1-6}$-alkyl, or $C_{2-6}$ hydroxyalkyl; mono-substituted, poly-substituted or unsubstituted variants of the following residues: $C_{3-8}$ cycloalkyl, —C(O)—$C_{5-6}$ aryl substituted with $C_{1-3}$ alkyl or halo, $C_{5-6}$ aryl, $C_{5-6}$ heteroaryl, $C_{5-6}$ cycloalkyl, and $C_{5-6}$ heterocycloalkyl;

any bond represented by a dashed and solid line represents a bond selected from the group consisting of a single bond and a double bond; and any carbon-carbon double bond has a configuration selected from the group consisting of cis and trans.

In some embodiments, the acid catalyst is selected from the group consisting of acetic acid, trifluoroacetic acid, methanesulfonic acid, p-toluenesulfonic acid, and trifluoromethanesulfonic acid. In one embodiment, the acid catalyst is p-toluenesulfonic acid. Those of skill in the art will recognize many other acid catalysts that may be suitable for use as a catalyst in the reaction described above.

In some embodiments, the enantiomeric excess produced by the reaction is greater than about 80% or greater than about 90%.

In some embodiments, $R_1$, $R_2$, and $R_3$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, arylalkyl, heteroarylalkyl; and mono-substituted, poly-substituted or unsubstituted variants of the following residues: cycloalkyl, cycloalkenyl, aryl, heteroaryl, or heterocycloalkyl. In some embodiments, $R_1$, $R_2$, and $R_3$ are separately selected from the group consisting of hydrogen; mono-substituted, poly-substituted or unsubstituted, straight or branched chain variants of the following residues: $C_1$-$C_{24}$ alkyl, arylalkyl, heteroarylalkyl; and mono-substituted, poly-substituted or unsubstituted variants of the following residues: cycloalkyl, aryl, heteroaryl, or heterocycloalkyl. In some embodiments, $R_1$, $R_2$, and $R_3$ are separately selected from the group consisting of hydrogen, methyl, methylene, and mono-substituted, poly-substituted or unsubstituted variants of the following residues:

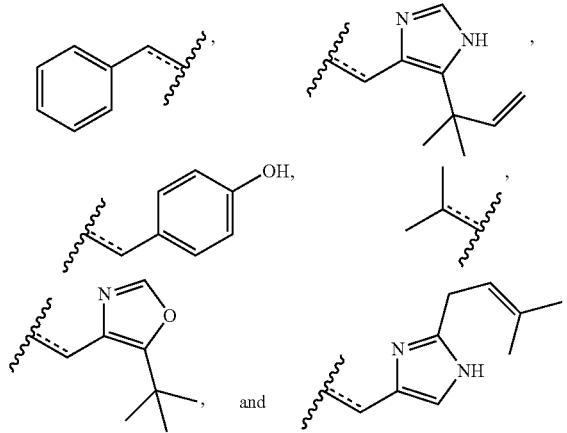

where the wavy lines indicate the point of attachment to the compound of formula I.

The term "halogen atom," as used herein, means any one of the radio-stable atoms of column 7 of the Periodic Table of the Elements, e.g., fluorine, chlorine, bromine, or iodine, with fluorine and chlorine being preferred.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R'are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxyl, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

The term "aromatic" refers to an aromatic group which has at least one ring have a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "alkyl," as used herein, means any unbranched or branched, substituted or unsubstituted, saturated hydrocarbon. The alkyl moiety, may be branched, straight chain, or cyclic. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is (are) one or more group(s) individually and independently selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heteroaryloxy, heterocyclyl, heterocyclooxy, heteroalicyclyl, hydroxyl, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substituent may be substituted with one of the above substituents.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

An "alkenyl" moiety refers to a group consisting of at least two carbon atoms and at least one carbon-carbon double bond. An alkenyl may be unbranched or branched, substituted or unsubstituted, unsaturated hydrocarbon including polyunsaturated hydrocarbons. In some embodiments, the alkenyl is a $C_1$-$C_6$ unbranched, mono-unsaturated or di-unsaturated, unsubstituted hydrocarbons. The term "cycloalkenyl" refers to any non-aromatic hydrocarbon ring, preferably having five to twelve atoms comprising the ring.

An "alkyne" moiety refers to a group consisting of at least two carbon atoms and at least one carbon-carbon triple bond.

Unless otherwise indicated, the substituent "R" appearing by itself and without a number designation refers to a substituent selected from the group consisting of alkyl, cycloalkyl, aryl, heteroaryl (bonded through a ring carbon) and heteroalicyclyl (bonded through a ring carbon).

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

An "O-carboxy" group refers to a RC(=O)O— group, where R is as defined herein.

A "C-carboxy" group refers to a —C(=O)OR groups where R is as defined herein.

An "acetyl" group refers to a —C(=O)CH$_3$, group.

A "trihalomethanesulfonyl" group refers to a $X_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a $X_3$CS(=O)$_2$NR— group with X and R as defined herein.

An "O-carbamyl" group refers to a —OC(=O)—NR, group-with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "acylalkyl" refers to a RC(=O)R'— group, with R as defined herein, and R' being a diradical alkylene group. Examples of acylalkyl, without limitation, may include CH$_3$C(=O)CH$_2$—, CH$_3$C(=O)CH$_2$CH$_2$—, CH$_3$CH$_2$C(=O)CH$_2$CH$_2$—, CH$_3$C(=O)CH$_2$CH$_2$CH$_2$—, and the like.

Unless otherwise indicated, when a substituent is deemed to be "optionally substituted," it is meant that the subsitutent is a group that may be substituted with one or more group(s) individually and independently selected from alkyl, alkenyl, alkynyl, cycloalkyl, aryl, heteroaryl, heteroalicyclic, hydroxyl, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is incorporated herein in its entirety.

The term "heterocyclyl" is intended to mean three-, four-, five-, six-, seven-, and eight- or more membered rings wherein carbon atoms together with from 1 to 3 heteroatoms constitute said ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Binding to the heterocycle can be at the position of a heteroatom or via a carbon atom of the heterocycle, or, for benzo-fused derivatives, via a carbon of the benzenoid ring.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxyl, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxyl, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxyl, cyano, O—$C_{1-6}$-alkyl, $C_{1-6}$-alkyl, hydroxyl-$C_{1-6}$-alkyl, and amino-$C_{1-6}$-alkyl.

In some embodiments, the compound of formula I is selected from the group consisting of the following compounds:

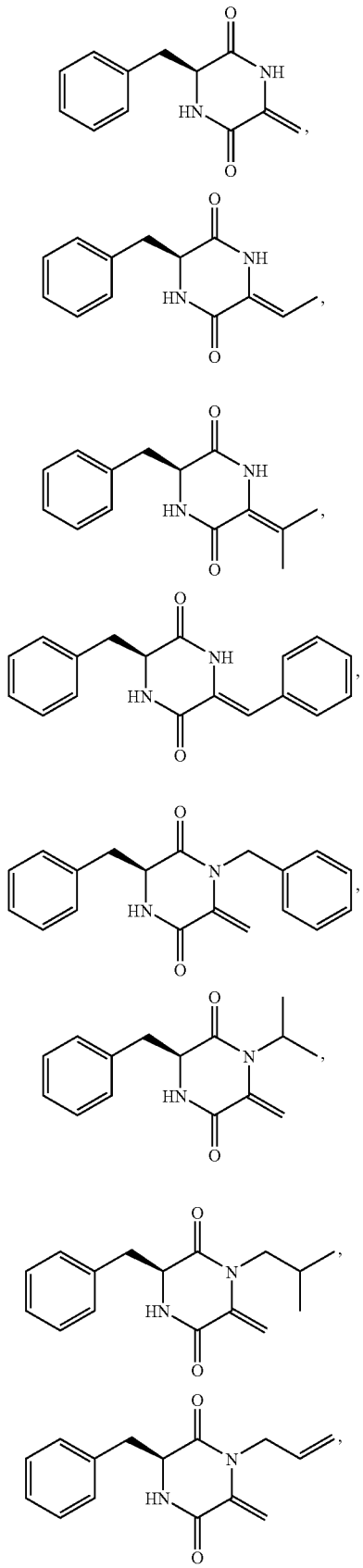

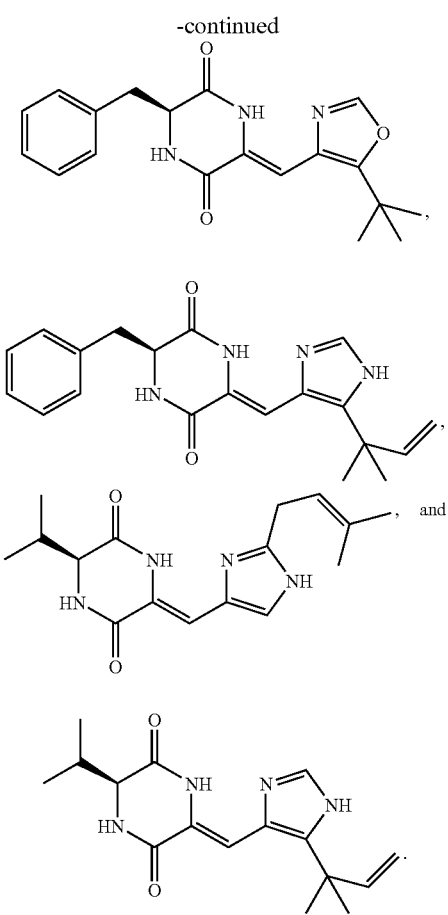

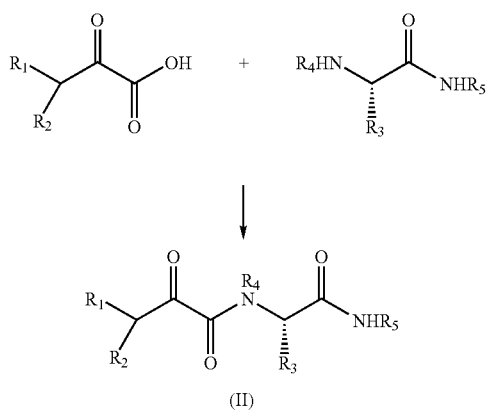

The reaction disclosed above may be carried out by refluxing the compound of formula II dissolved in a suitable solvent such as trichloroethylene or toluene with a catalytic amount of the acid catalyst. Those of skill in the art will appreciate that a variety of solvents, identity and amount of catalyst, and reaction conditions may be used and that these variables can be selected by simple optimization.

In one non-limiting embodiment, the compound of formula II is synthesized by condensation of an α-keto acid with an α-amino amide. Thus, for example, the following reaction may be carried out:

The above reaction may be carried out in the presence of agents suitable to promote the condensation. In one non-limiting example, the reaction is carried out in the presence of ethylene dichloride and butanol. An appropriate solvent may be used, such as dimethylformamide or dichloromethane.

The α-keto acid starting material may be synthesized according to the following synthetic scheme:

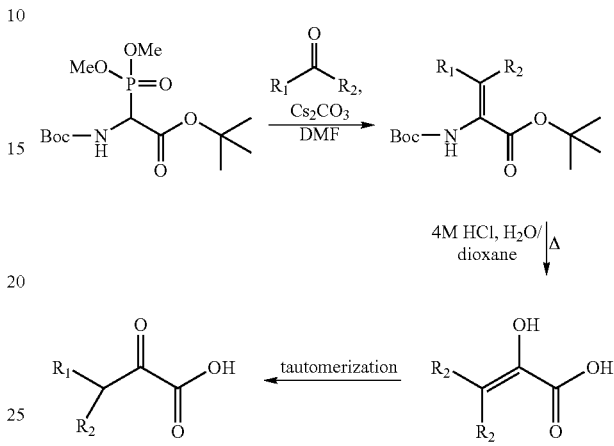

Those of skill in the art will appreciate other suitable methods for synthesizing the α-keto acid starting material.

EXAMPLES

Example 1a

N-2-oxo-propanoyl-L-phenylalanine amide

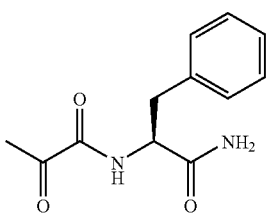

A suspension of HCl.H-Phe-NH$_2$ (1.0 g, 4.98 mmol) in DCM (49 mL) was neutralized with Et$_3$N (0.69 mL, 4.98 mmol) at 4° C. To this mixture were added HOBt.H$_2$O (0.76 g, 4.98 mmol), pyruvic acid (0.52 mL, 7.47 mmol), and EDC.HCl (1.05 g, 5.47 mmol), and the mixture was stirred at 4° C. for 30 min and at room temperature for 2 h. After removal of the solvent in vacuo, the residue was dissolved in AcOEt, successively washed with 10% citric acid, 5% NaHCO$_3$ and saturated NaCl for three times, dried over Na$_2$SO$_4$, and concentrated in vacuo to obtain 0.76 g (65%) of the title compound as a white solid: mp 138-140° C.; $^1$H NMR (300 MHz, DMSO-d$_6$) δ 8.34 (d, J=8.6 Hz, 1H), 7.52 (s, 1H), 7.24-7.19 (m, 6H), 4.45-4.37 (m, 1H), 3.11 (dd, J=4.2, 13.8 Hz, 1H), 2.96 (dd, J=9.5, 13.8 Hz, 1H), 2.26 (s, 3H); HRMS (EI): m/z 234.1008 (M$^+$) (calcd for C$_{12}$H$_{14}$N$_2$O$_3$: 234.1004).

Example 1b

N-2-oxo-butanoyl-L-phenylalanine amide

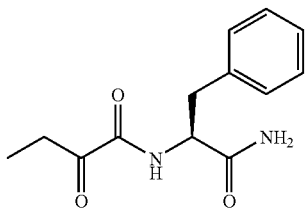

The title compound was prepared according to the same procedure as described in Example 1a using 2-oxobutanoic acid instead of pyruvic acid. White solid (94%); mp 121-123° C.; $^1$H NMR (300 MHz, DMSO-$d_6$) δ 8.35 (d, J=8.5 Hz, 1H), 7.53 (s, 1H), 7.24-7.19 (m, 6H), 4.43 (ddd, J=4.4, 8.5, 9.6 Hz, 1H), 3.10 (dd, J=4.5, 13.8 Hz, 1H), 2.96 (dd, J=9.6, 13.8 Hz, 1H), 2.72 (q, J=7.2 Hz, 2H), 0.92 (t, J=7.2 Hz, 3H); HRMS (EI): m/z 248.1157 (M$^+$) (calcd for $C_{13}H_{16}N_2O_3$: 248.1161).

Example 1c

N-2-oxo-3-methylbutanoyl-L-phenylalanine amide

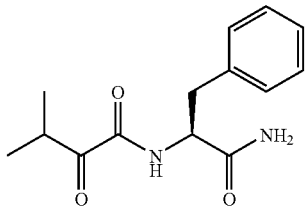

The title compound was prepared according to the same procedure as described in Example 1a using 3-methyl-2-oxobutanoic acid instead of pyruvic acid. White solid (74%); mp 166-168° C.; $^1$H NMR (300 MHz, DMSO-$d_6$) δ 8.41 (d, J=8.7 Hz, 1H), 7.55 (s, 1H), 7.24-7.19 (m, 6H), 4.50 (ddd, J=4.2, 8.7, 9.9 Hz, 1H), 3.23 (dq, J=6.9, 6.9 Hz, 1H), 3.10 (dd, J=4.2, 13.6 Hz, 1H), 2.92 (dd, J=9.9, 13.6 Hz, 1H), 0.96 (d, J=6.9 Hz, 3H), 0.87 (d, J=6.9 Hz, 3H); HRMS (EI): m/z 262.1311 (M$^+$) (calcd for $C_{14}H_{18}N_2O_3$: 262.1317).

Example 1d

N-2-oxo-3-phenylpropanoyl-L-phenylalanine amide

The title compound was prepared according to the same procedure as described in Example 1a using 3-phenyl-2-oxobutanoic acid instead of pyruvic acid. White solid 66%; mp 123-125° C.; $^1$H NMR (300 MHz, CDCl$_3$) δ 7.57 (d, J=7.7 Hz, 1H), 7.34-7.01 (m, 10H), 5.83 (s, 1H), 5.75 (s, 1H), 4.61 (ddd, J=6.9, 6.9, 7.7 Hz, 1H), 4.15 (s, 2H), 3.08 (dd, J=2.0, 6.9 Hz, 2H); HRMS (EI): m/z 310.1318 (M$^+$) (calcd for $C_{18}H_{18}N_2O_3$: 310.1317).

Example 2a (S)-3-benzyl-6-methylenepiperazine-2,5-dione

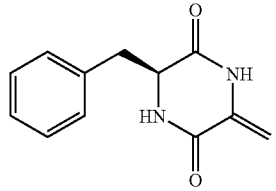

Using a Dean-Stark trap whose trap part was filled with molecular sieves 3A, a solution of N-2-oxo-propanoyl-L-phenylalanine amide from Example 1a (100 mg, 0.427 mmol) in toluene (20 mL) was refluxed in the presence of p-TsOH.H$_2$O (4.37 mg, 0.023 mmol, 0.05 eq) for 18 h. After removal of the solvent, the residue was triturated in ether to obtain 89 mg (96%) of the title compound as a white solid: mp 175-177° C. (decomp); $^1$H NMR (300 MHz, DMSO-$d_6$) δ 10.36 (s, 1H), 8.41 (s, 1H), 7.24-7.11 (m, 5H), 4.90 (s, 1H), 4.50 (s, 1H), 4.40-4.37 (m, 1H), 3.15 (dd, J=3.8, 13.5 Hz, 1H), 2.91 (dd, J=5.0, 13.5 Hz, 1H); HRMS (EI): m/z 216.0891(M$^+$) (calcd for $C_{12}H_{12}N_2O_2$: 216.0899). Enantiomeric excess was determined to be >99% using chiral HPLC with a CHIRALCEL OD column.

Example 2b (S,Z)-3-benzyl-6-ethylidenepiperazine-2,5-dione

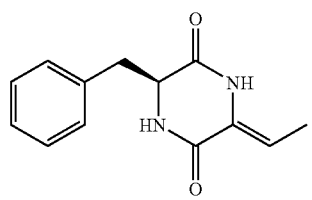

The title compound was prepared according to Example 2a using the compound of Example 1b. White solid (86%); mp 219-221° C. (decomp); $^1$H NMR (300 MHz, DMSO-$d_6$) δ 9.75 (s, 1H), 8.20 (s, 1H), 7.25-7.12 (m, 5H), 5.50 (q, J=7.5 Hz, 1H), 4.32-4.29 (m, 1H), 3.12 (dd, J=4.2, 13.5 Hz, 1H), 2.90 (dd, J=5.0, 13.5 Hz, 1H), 1.52 (d, J=7.5 Hz, 3H); HRMS (EI): m/z 230.1057 (M$^+$) (calcd for $C_{13}H_{14}N_2O_2$: 230.1055); $[α]_D^{26}$ −111.1 (c=1.03, DMSO). Enantiomeric excess was determined to be >99% using chiral HPLC with a CHIRALCEL OD column.

Example 2c (S)-3-benzyl-6-(propan-2-ylidene)piperazine-2,5-dione

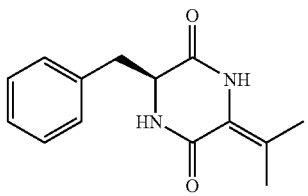

The title compound was prepared according to Example 2a using the compound of Example 1c. White solid (94%); mp 255-257° C. (decomp); $^1$H NMR (300 MHz, DMSO-$d_6$) δ 9.26 (s, 1H), 7.97 (d, J=3.3 Hz, 1H), 7.56-7.10 (m, 5H), 4.04 (m, 1H), 3.00 (dd, J=4.4, 13.5 Hz, 1H), 2.85 (dd, J=5.3, 13.5 Hz, 1H), 1.8 (s, 3H), 1.49 (s, 3H);

HRMS (EI): m/z 244.1210(M$^+$) (calcd for $C_{14}H_{16}N_2O_2$: 244.1212). Enantiomeric excess was determined to be >99% using chiral HPLC with a CHIRALCEL OD column.

Example 2d (S,Z)-3-benzyl-6-benzylidenepiperazine-2,5-dione

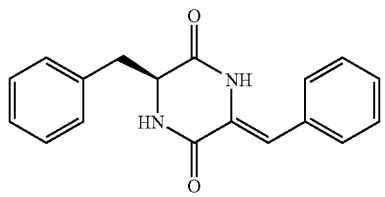

The title compound was prepared according to Example 2a using the compound of Example 1d. Off white solid (35%); mp 275-276° C.; $^1$H NMR (300 MHz, DMSO-$d_6$) δ 9.75 (s, 1H), 8.46 (s, 1H), 7.46-7.13 (m, 10H), 6.33 (s, 1H), 4.36 (m, 1H), 3.15 (dd, J=3.9, 13.4 Hz, 1H), 2.95 (dd, J=4.9, 13.4 Hz, 1H); HRMS (EI): m/z 292.1211(M$^+$) (calcd for $C_{18}H_{16}N_2O_2$: 292.1212); $[α]_D^{25}$ −316.2 (c=0.62, DMSO). Enantiomeric excess was determined to be 72.5% using chiral HPLC with a CHIRALCEL OD column.

Example 3a

N-2-oxo-propanoyl-L-phenylalanine benzylamide (3a)

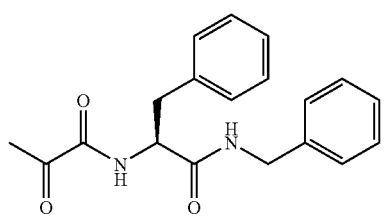

A solution of HCl.H-Phe-NH-benzyl (1.93 g, 6.64 mmol) in DMF was neutralized with Et$_3$N (0.92 mL, 6.64 mmol) at 4° C. To this mixture were added HOBt.H$_2$O (0.99 g, 6.46 mmol), pyruvic acid (0.69 mL, 9.99 mmol) and EDC.HCl (1.26 g, 6.64 mmol), and the mixture was stirred at room temperature for 2 h. After removal of the solvent in vacuo, the residue was dissolved in AcOEt, successively washed with 10% citric acid, 5% NaHCO$_3$ and saturated NaCl for three times, dried over Na$_2$SO$_4$, and concentrated in vacuo. The residual oil was purified by a silica gel column chromatography to yield 0.61 g (30%) of title compound as a colorless oil. $^1$H NMR (300 MHz, CDCl$_3$) δ 7.52 (d, J=8.4 Hz, 1H), 7.27-7.03 (m, 10H), 5.80 (br s, 1H), 4.48-4.58 (m, 1H), 4.24-4.41 (m, 2H), 3.01-3.18 (m, 2H), 2.49 (s, 3H); HRMS (EI): m/z 324.1470 (M$^+$) (calcd for $C_{19}H_{20}N_2O_3$: 324.1474); $[α]_D^{26}$ −13.3 (c=1.06, CHCl$_3$).

Example 3b

N-2-oxo-propanoyl-L-phenylalanine isopropylamide

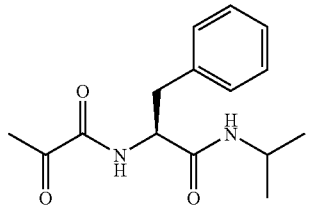

The title compound was prepared according to Example 3a using HCl.H-Phe-NH-isopropyl. 73% yield; $^1$H NMR (300 MHz, CDCl$_3$) δ 7.57 (d, J=7.2 Hz, 1H), 7.21-7.34 (m, 5H), 5.09 (d, J=7.0 Hz 1H), 4.36-4.45 (m, 1H), 3.88-4.01 (m, 1H), 3.13 (dd, J=5.9, 13.4 Hz, 1H), 2.97 (dd, J=9.0, 13.4 Hz, 1H), 2.46 (s, 3H), 1.03 (d, J=6.6 Hz 3H), 0.91 (d, J=6.6 Hz 3H); HRMS (EI): m/z 276.1472 (M$^+$) (calcd for $C_{15}H_{20}N_2O_3$: 276.1474); $[α]_D^{25}$ −14.8 (c=1.05, CHCl$_3$).

Example 3c

N-2-oxo-propanoyl-L-phenylalanine isobutylamide

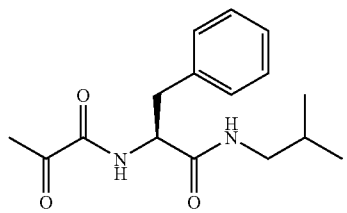

The title compound was prepared according to Example 3a using HCl.H-Phe-NH-isobutyl. 57% yield; $^1$H NMR (300 MHz, CDCl$_3$) δ 7.52 (d, J=8.1 Hz, 1H), 7.20-7.34 (m, 5H), 5.46 (br s, 1H), 4.47 (ddd, J=6.3, 8.1, 8.4 Hz, 1H), 3.12 (dd, J=6.3, 13.5 Hz, 1H), 3.04 (dd, J=8.4, 13.5 Hz, 1H), 2.89-3.04 (m, 2H), 2.45 (s, 3H), 1.54-1.67 (m, 1H), 0.76 (d, J=6.8 Hz, 3H), 0.74 (d, J=6.8 Hz, 3H); HRMS (EI): m/z 290.1636 (M⁺) (calcd for C₁₆H₂₂N₂O₃: 290.1630); [α]_D²⁶ −23.9 (c=1.03, CHCl₃).

Example 3d

N-2-oxo-propanoyl-L-phenylalanine allylamide

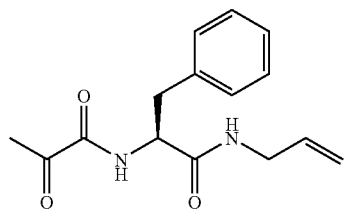

The title compound was prepared according to Example 3a using HCl.H-Phe-NH-allyl. 40% yield; ¹H NMR (300 MHz, CDCl₃) δ 7.51 (br d, J=8.4 Hz, 1H), 7.34-7.19 (m, 5H), 5.71-5.55 (m, 1H), 5.58 (br s, 1H), 5.09-4.96 (m, 2H), 4.55-4.47 (m, 1H), 3.81-3.75 (m, 2H), 3.17-3.02 (m, 2H), 2.44 (s, 3H); HRMS (EI): m/z 274.1325 (M⁺) (calcd for C₁₅H₁₈N₂O₃: 274.1317); [α]_D²⁶ −26.1 (c=1.00, CHCl₃).

Example 4a (S)-1,3-Dibenzyl-6-methylenepiperazine-2,5-dione

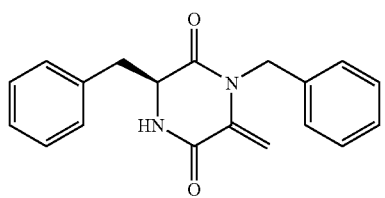

Using a Dean-Stark trap whose trap part was filled with molecular sieves 3A, a solution of N-2-oxo-propanoyl-L-phenylalanine benzylamide from Example 3a (100 mg, 0.31 mmol) in toluene (20 mL) was refluxed in the presence of p-TsOH.H₂O (1.8 mg, 0.0093 mmol, 0.03 eq) for 24 h. After removal of the solvent, the residue was purified by a silica gel chromatography to yield 50 mg (53%) of title compound as a white solid: mp 124-127° C., ¹H NMR (300 MHz, CDCl₃) δ 7.01-7.35 (m, 10H), 6.84 (br s, 1H), 5.60 (s, 1H), 5.01 (d, J=15.7 Hz, 1H), 4.85 (d, J=15.7 Hz, 1H), 4.76 (s, 1H), 4.49-4.52 (m, 1H), 3.36 (dd, J=3.7, 13.6 Hz, 1H), 3.12 (dd, J=7.7, 13.6 Hz, 1H); HRMS (EI): m/z 306.1369 (M⁺) (calcd for C₁₉H₁₈N₂O₂: 306.1368). Enantiomeric excess was determined to be >99% using chiral HPLC with a CHIRALCEL OD column.

Example 4b (S)-3-Benzyl-1-isopropyl-6-methylenepiperazine-2,5-dione

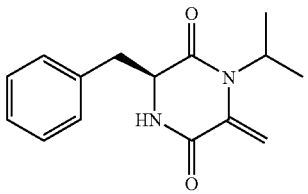

The title compound was prepared according to Example 4a using the compound from Example 3b. 20% yield; mp 141-142° C. Enantiomeric excess was determined to be >99% using chiral HPLC with a CHIRALCEL OD column.

Example 4c (S)-3-Benzyl-1-isobutyl-6-methylenepiperazine-2,5-dione

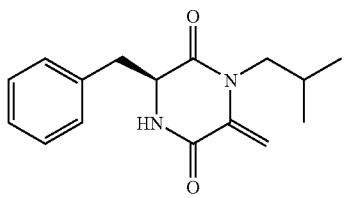

The title compound was prepared according to Example 4a using the compound from Example 3c. 43% yield; HRMS (EI): m/z 324.1470(M⁺) (calcd for C₁₉H₂₀N₂O₃: 324.1474). ¹H NMR (300 MHz, CDCl₃) δ 7.17-7.36 (m, 5H), 5.91 (br s, 1H), 5.73 (d, J=1.5 Hz, 1H), 4.84 (s, 1H), 4.30-4.37 (m, 1H), 3.65 (dd, J=8.1, 13.8 Hz, 1H), 3.55 (dd, J=6.9, 13.8 Hz, 1H), 3.37 (dd, J=3.6, 13.8 Hz, 1H), 2.93 (dd, J=9.0, 13.5 Hz, 1H), 1.98-2.13 (m, 1H), 0.92 (d, J=5.7 Hz, 3H), 0.90 (d, J=5.7 Hz, 3H). Enantiomeric excess was determined to be >99% using chiral HPLC with a CHIRALCEL OD column.

Example 4d (S)-1-Allyl-3-benzyl-6-methylenepiperazine-2,5-dione

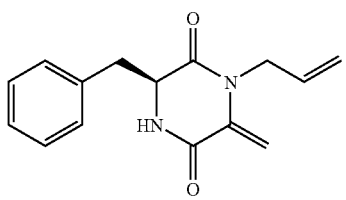

The title compound was prepared according to Example 4a using the compound from Example 3d. 92% yield; mp 102-110° C.; HRMS (EI): m/z 256.1210 (M⁺) (calcd for C₁₅H₁₆N₂O₂: 256.1212). ¹H NMR (300 MHz, CDCl₃) δ 7.16-

7.35 (m, 5H), 6.48 (br s, 1H), 5.63-5.77 (m, 1H), 5.65 (s, 1H), 5.21 (d, J=10.2 Hz, 1H), 5.10 (d, J=17.4 Hz, 1H), 4.84 (s, 1H), 4.36-4.48 (m, 2H), 4.25 (br d, J=16.2 Hz, 1H), 3.27-3.38 (m, 1H), 2.94-3.08 (m, 1H). Enantiomeric excess was determined to be >99% using chiral HPLC with a CHIRALCEL OD column.

Example 5 tert-Butyl 1-(tert-butoxycarbonyl)-2-(5-tert-butyloxazol-4-yl)vinylcarbamate

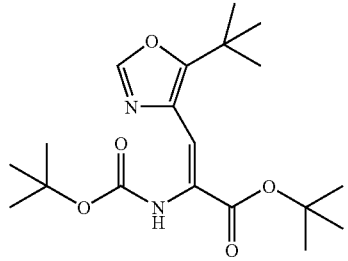

To a solution of N-(tert-Butoxycarbonyl)-α-dimethylphosphonoglycine-tert-butyl ester (11.8 g, 34.68 mmol) and 5-tert-butyloxazole-4-carboxaldehyde (6.9 g, 45.08 mmol) in DMF (50 mL) was added $Cs_2CO_3$ (12.4 g, 38.15 mmol) under an argon atmosphere at room temperature. The reaction mixture was stirred for 14 h at room temperature. After removal of solvent in vacuo, the residue was dissolved in AcOEt, successively washed with 10% citric acid, 5% $NaHCO_3$ and saturated NaCl for three times, dried over $Na_2SO_4$, and concentrated in vacuo. The residual oil was purified by a silica gel column chromatography to yield 6.0 g (47%) of title compound as a white solid: mp 170-172° C.; $^1$H NMR (300 MHz, $CDCl_3$) δ 7.74 (s, 1H), 6.55 (s, 1H), 1.54 (s, 9H), 1.49 (s, 9H), 1.38 (s, 9H); HRMS (EI): m/z 366.2159 ($M^+$) (calcd for $C_{19}H_{30}N_2O_5$: 366.2154).

Example 6

3-(5-tert-Butyloxazol-4-yl)-2-hydroxyacrylic acid

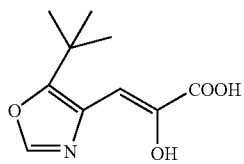

The compound from Example 5 (6.0 g, 16.3 mmol) was treated with 4N HCl-dioxane (64 mL) for 1 h at room temperature. After removal of the solvent, the residue was dissolved in AcOEt, washed with 5% citric acid and saturated NaCl, dried over $Na_2SO_4$, and concentrated in vacuo to obtain 2.6 g (76%) of the title compound as a white solid: mp 153-155° C.; $^1$H NMR (300 MHz, DMSO-$d_6$) δ 8.59 (s, 1H), 6.55 (s, 1H), 1.36 (s, 1H); m/z 211.0841 ($M^+$) (calcd for $C_{10}H_{13}NO_4$: 211.0844).

Example 7

3-(5-tert-Butyloxazol-4-yl)-N-((S)-1-carbamoyl-2-phenylethyl)-2-hydroxyacrylamide

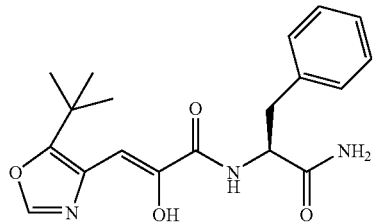

To a solution of the compound from Example 6 (2.61 g, 12.3 mmol) in DMF were added HOBt.$H_2O$ (2.26 g, 14.76 mmol), EDC.HCl (2.8 g, 14.76 mmol), HCl.H-Phe-$NH_2$ (3.16 g, 14.76 mmol) and $Et_3N$ (1.72 mL, 12.3 mmol) and the reaction mixture was stirred for 14 h at room temperature. After removal of the solvent, the residue was dissolved in AcOEt, successively washed with 10% citric acid, 5% $NaHCO_3$ and saturated NaCl for three times, dried over $Na_2SO_4$, and concentrated in vacuo to obtain the title compound: yield 2.26 g (43%); mp 50-53° C., $^1$H NMR (300 MHz, $CDCl_3$) δ 11.04 (s, 1H), 7.81 (d, J=0.6 Hz 1H), 7.74-7.21 (m, 5H), 6.62 (d, J=0.7 Hz 1H), 6.00 (s, 1H), 5.52 (s, 1H), 4.79-4.72 (m, 1H), 3.24-3.11 (m, 2H), 1.38 (s, 9H); HRMS (EI): m/z 357.1689 ($M^+$) (calcd for $C_{19}H_{23}N_3O_4$: 357.1688).

Example 8

(S,Z)-3-[(5-tert-Butyloxazol-4-yl)methylene]-6-benzylpiperazine-2,5-dione

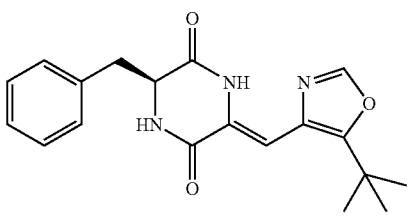

Using a Dean-Stark trap whose trap part was filled with molecular sieves 3A, a solution of the compound from Example 7 (50 mg, 0.14 mmol) in toluene (20 mL) was refluxed in the presence of p-TsOH (0.8 mg, 0.0042 mmol) for 18 h. After removal of the solvent, the residue was purified by HPLC to obtain the title compound: yield 11.5 mg (23%), mp 52-56° C., $^1$H NMR (300 MHz, DMSO-$d_6$) δ 10.65 (s, 1H), 8.60 (s, 1H), 8.47 (s, 1H), 7.24-7.13 (m, 5H), 6.37 (s, 1H), 4.52 (m, 1H), 3.20 (dd, J=3.7, 13.6 Hz, 1H), 2.95 (dd, J=5.0, 13.6 Hz, 1H), 1.31 (s, 9H); HRMS (EI): m/z 339.1584 ($M^+$) (calcd for $C_{19}H_{21}N_3O_3$: 339.1583); $[α]_D^{25}$ −128.9 (c=0.27, DMSO). Enantiomeric excess was determined to be 98% using chiral HPLC with a CHIRALCEL OD column.

Example 9

Synthesis of α-Keto Acid Oxazole Derivatives

Three other α-keto acid compounds were synthesized using the same procedure as in Examples 5 and 6 using thiazole-2-carboxaldehyde, 5-methylfuran-2-carboxaldehyde, and thiophene-2-carboxaldehyde instead of 5-tert-butyloxazole-4-carboxaldehyde. Yields of step 1 (according to Example 5) and step 2 (according to Example 6) were (87%, 34%), (84%, 92%), and (71%, 96%) respectively.

Example 10

Effect of Acid Catalyst on Cyclization Reaction (S)-1-Allyl-3-benzyl-6-methylenepiperazine-2,5-dione was prepared from N-2-oxo-propanoyl-L-phenylalanine allylamide by reaction with acetic acid (10% solution), trifluoroacetic acid (10% solution), methanesulfonic acid (3 mol %), p-toluenesulfonic acid (3 mol %), and trifluoromethanesulfonic acid (3 mol %). Enantiomeric excess of the product was determined by chiral HPLC using a CHIRALCEL OD column eluted with n-Hexane:Ethanol (5:1). The product yields and enantiomeric excess values are presented in Table 1.

TABLE 1

Effect of Acid Catalyst on Cyclization Reaction.

| Acid Catalyst | Yield (%) | Enantiomeric Excess (%) |
|---|---|---|
| acetic acid | N.D. (7)[a] | N.D. |
| trifluoroacetic acid | 62 (82)[a] | >99 |
| methanesulfonic acid | N.D. (1)[a] | N.D. |
| p-toluenesulfonic acid | 92 | >99 |
| trifluoromethanesulfonic | 42 (85)[a] | >99 |

[a]The values in parentheses indicate HPLC yield.

Example 11

Effect of TFA Amount on Cyclization Reaction

The effect of the amount of TFA acid catalyst was evaluated. (S)-1-Allyl-3-benzyl-6-methylenepiperazine-2,5-dione was prepared by reacting N-2-oxo-propanoyl-L-phenylalanine allylamide with various amounts of trifluoroacetic acid for 24 hours. Enantiomeric excess of the product was determined by chiral HPLC using a CHIRALCEL OD column eluted with n-Hexane:Ethanol (5:1). The TFA amounts, product yields, and enantiometric excess presented in Table 2.

TABLE 2

Effect of TFA Amount on Cyclization Reaction.

| TFA (% soln.) | Yield (%) | Enantiomeric Excess (%) |
|---|---|---|
| 0.06 | N.D. (0.3)[a] | N.D. |
| 0.5 | N.D. (1)[a] | N.D. |
| 1 | 26 (47)[a] | >99 |
| 5 | 42 (76)[a] | >99 |
| 10 | 62 (82)[a] | >99 |

[a]The values in parentheses indicate HPLC yield.

Example 12

Effect of Reaction Conditions on (S,Z)-3-benzyl-6-benzylidenepiperazine-2,5-dione Production The effect of the amount of acid catalyst and reaction time was evaluated. (S,Z)-3-benzyl-6-benzylidenepiperazine-2,5-dione was prepared by reacting N-2-oxo-3-phenylpropanoyl-L-phenylalanine amide with various amounts of p-toluenesulfonic acid for various times. Enantiomeric excess of the product was determined by chiral HPLC using a CHIRALCEL OD column eluted with n-Hexane:Ethanol (5:1). The reaction conditions, product yields, and enantiomeric excess is presented in Table 3.

TABLE 3

Effect of Reaction Conditions on Cyclization Reaction.

| Amount p-TsOH (mol %) | Time (h) | Yield (%) | Enantiomeric Excess (%) |
|---|---|---|---|
| 1 | 18 | 20 | >99 |
| 1 | 48 | 31 | >99 |
| 5 | 6 | 34 | >99 |
| 5 | 18 | 35 | 72.5 |
| 10 | 3 | 5 | >99 |
| 10 | 6 | 38 | 59 |

Example 13

Effect of Reaction Conditions on (S,Z)-3-[(5-tert-Butyloxazol-4-yl)methylene]-6-benzylpiperazine-2,5-dione Production The effect of the amount of acid catalyst and reaction time was evaluated. (S,Z)-3-[(5-tert-Butyloxazol-4-yl)methylene]-6-benzylpiperazine-2,5-dione was prepared by reacting 3-(5-tert-Butyloxazol-4-yl)-N-((S)-1-carbamoyl-2-phenylethyl)-2-hydroxyacrylamide with various amounts of p-toluenesulfonic acid for various times. Enantiomeric excess of the product was determine by chiral HPLC using a CHIRALCEL OD column eluted with n-Hexane:Ethanol (5:1). The reaction conditions, product yields, and enantiomeric excess is present is Table 4.

TABLE 4

Effect of Reaction Conditions on Cyclization Reaction.

| Amount p-TsOH (mol %) | Time (h) | Yield (%) | Enantiomeric Excess (%) |
|---|---|---|---|
| 1 | 12 | 8 | 99 |
| 1 | 18 | 14 | 98 |
| 3 | 6 | 17 | 98 |
| 3 | 18 | 23 | 98 |
| 5 | 6 | 20 | 99 |
| 5 | 18 | 38 | 94 |

The results indicate that racemization can be minimized with significant yield at p-TsOH amount of 5 mol % and a reaction time of 6 hours.

Although the invention has been described with reference to embodiments and examples, it should be understood that numerous and various modifications can be made without departing from the spirit of the invention. Accordingly, the invention is limited only by the following claims.

What is claimed is:

1. A method of preparing a compound of formula I:

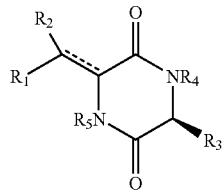

comprising reacting an acid catalyst with a compound of formula II in such a manner so as to produce the compound of formula I with an enantiomeric excess greater than about 50%:

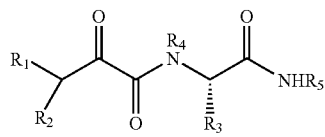

wherein:

$R_1$, $R_2$, and $R_3$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, alkoxy, acyl, arylalkyl, heteroarylalkyl, alkyloxycarbonyloxy, ester, arylalkoxy, and alkylthio; and mono-substituted, poly-substituted or unsubstituted variants of the following residues: acyloxy, aryloxycarbonyloxy, cycloalkyl, cycloalkenyl, cycloalkoxy, aryl, heteroaryl, heterocycloalkyl, carbonyl, carbonylacyl, amino, aminocarbonyl, amide, aminocarbonyloxy, nitro, azido, phenyl, hydroxyl, arylthio, oxysulfonyl, carboxy, and cyano;

$R_4$ and $R_5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, aryl-$C_{1-6}$-alkyl, and $C_{2-6}$ hydroxyalkyl; and mono-substituted, poly-substituted and unsubstituted variants of the following residues: $C_{3-8}$ cycloalkyl, —C(O)—$C_{5-6}$ aryl substituted with $C_{1-3}$ alkyl or halo, $C_{5-6}$ aryl, $C_{5-6}$ heteroaryl, $C_{5-6}$ cycloalkyl, and $C_{5-6}$ heterocycloalkyl;

any bond represented by a dashed and solid line represents a bond selected from the group consisting of a single bond and a double bond; and any carbon-carbon double bond has a configuration selected from the group consisting of cis and trans.

2. The method of claim 1, wherein the acid catalyst is selected from the group consisting of acetic acid, trifluoroacetic acid, methanesulfonic acid, p-toluenesulfonic acid, and trifluoromethanesulfonic acid.

3. The method of claim 1, wherein the enantiomeric excess is greater than about 80%.

4. The method of claim 1, wherein the enantiomeric excess is greater than about 90%.

5. The method of claim 1, wherein $R_1$, $R_2$, and $R_3$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, $C_2$-$C_{24}$ alkynyl, arylalkyl, and heteroarylalkyl; and mono-substituted, poly-substituted or unsubstituted variants of the following residues: cycloalkyl, cycloalkenyl, aryl, heteroaryl, and heterocycloalkyl.

6. The method of claim 5, wherein $R_1$, $R_2$, and $R_3$ are separately selected from the group consisting of hydrogen; mono-substituted, poly-substituted or unsubstituted, straight or branched chain variants of the following residues: $C_1$-$C_{24}$ alkyl, arylalkyl, and heteroarylalkyl; and mono-substituted, poly-substituted or unsubstituted variants of the following residues: cycloalkyl, aryl, heteroaryl, and heterocycloalkyl.

7. The method of claim 6, wherein $R_1$, $R_2$, and $R_3$ are separately selected from the group consisting of hydrogen, methyl, methylene, and mono-substituted, poly-substituted or unsubstituted variants of the following residues:

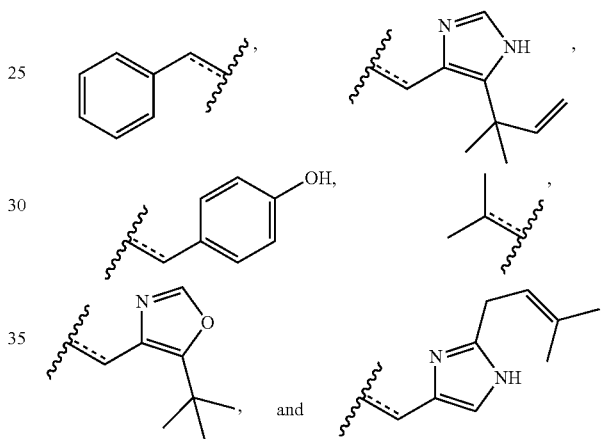

8. The method of claim 7, wherein the compound of formula I is selected from the group consisting of:

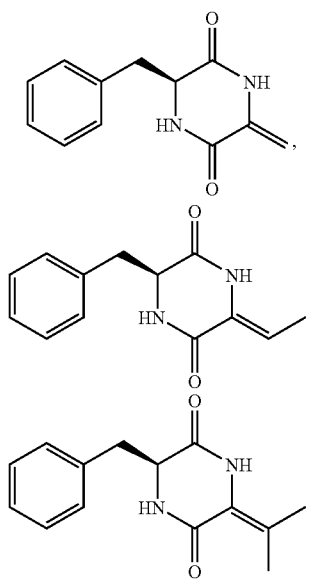

-continued
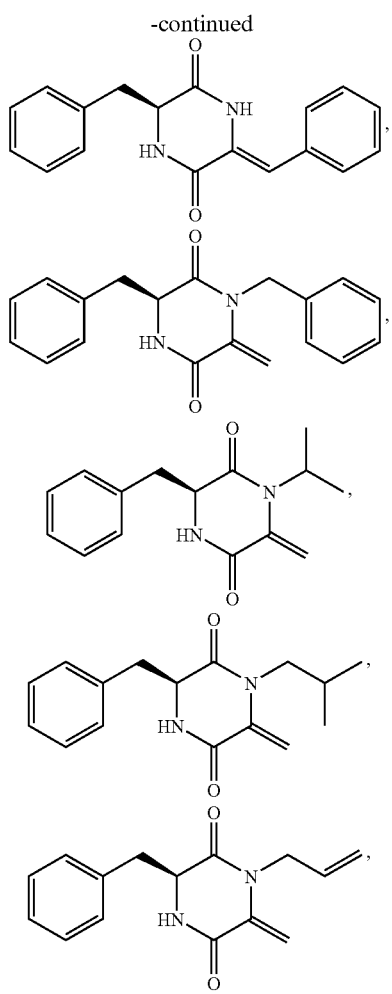
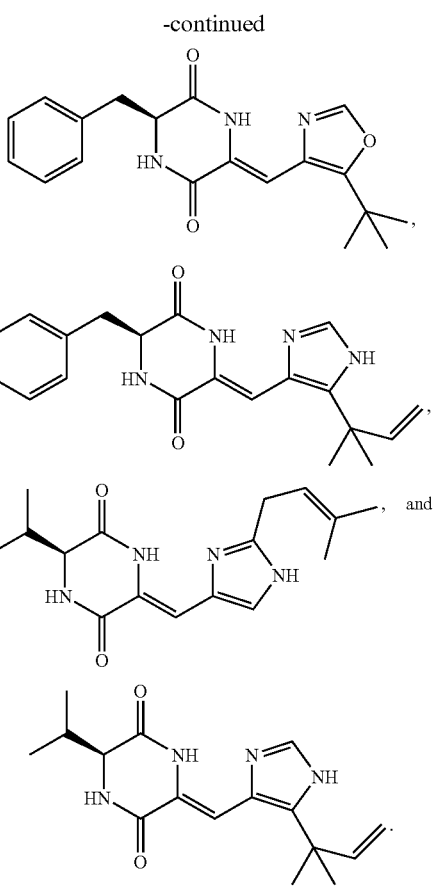
* * * * *

UNITED STATES PATENT AND TRADEMARK OFFICE
CERTIFICATE OF CORRECTION

PATENT NO. : 7,732,605 B2
APPLICATION NO. : 11/390326
DATED : June 8, 2010
INVENTOR(S) : Yoshio Hayashi It is certified that error appears in the above-identified patent and that said Letters Patent is hereby corrected as shown below:

At Column 1, Line 52, change "Bioorg" to --Bioorg.--.

At Column 8, Line 10, change "have" to --having--.

At Column 9, Line 1, change "substitutent" to --substituent--.

At Column 10, Line 9, change "substitutent" to --substituent--.

At Column 11, Line 56, change "quionoline," to --quinoline,--.

At Column 20, Line 67, change "$_{15}H_{16}N_2O_2$:" to --$C_{15}H_{16}N_2O_2$:--.

At Column 22, Line 33, change "(calced" to --(calcd--.

At Column 23, Line 54 (Approx.), change "enantiometric" to --enantiomeric--.

At Column 23, Line 54 (Approx.), after "excess" insert --is--.

At Column 24, Line 11-12, change "Enantiometric" to --Enantiomeric--.

At Column 24, Line 43, change "determine" to --determined--.

At Column 24, Line 46, change "present is" to --presented in--.

At Column 24, Line 61, after "at" insert --a--.

At Column 25, Line 43, Claim 1, change "mono -substituted," to --mono-substituted,--.

At Column 26, Line 1, Claim 5, change "poly -substituted" to --poly-substituted--.

At Column 26, Line 4-5, Claim 5, change "poly -substituted" to --poly-substituted--.

Signed and Sealed this
Thirteenth Day of September, 2011

David J. Kappos
*Director of the United States Patent and Trademark Office*